US011732230B2

United States Patent
Chen et al.

(10) Patent No.: US 11,732,230 B2
(45) Date of Patent: Aug. 22, 2023

(54) BIOMIMETIC SYSTEM

(71) Applicant: National Chiao Tung University, Hsinchu (TW)

(72) Inventors: Guan-Yu Chen, Hsinchu County (TW); Jia-Wei Yang, Taoyuan (TW); Ko-Chih Lin, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 556 days.

(21) Appl. No.: 16/899,109

(22) Filed: Jun. 11, 2020

(65) Prior Publication Data

US 2021/0238522 A1 Aug. 5, 2021

(30) Foreign Application Priority Data

Feb. 4, 2020 (TW) .................................. 109103354

(51) Int. Cl.
*C12M 1/00* (2006.01)
*C12M 3/06* (2006.01)
*G01N 33/50* (2006.01)

(52) U.S. Cl.
CPC ............ *C12M 23/16* (2013.01); *C12M 29/04* (2013.01); *C12M 29/14* (2013.01); *G01N 33/5008* (2013.01)

(58) Field of Classification Search
CPC ...... C12M 23/16; C12M 29/04; C12M 29/14; C12M 41/46; G01N 33/5008; G01N 33/5064

See application file for complete search history.

(56) References Cited

U.S. PATENT DOCUMENTS

| | | | |
|---|---|---|---|
| 9,791,433 B2 | 10/2017 | Marx | |
| 2003/0150445 A1* | 8/2003 | Power | A61M 16/049 128/200.14 |
| 2011/0117538 A1* | 5/2011 | Niazi | C12M 29/06 435/5 |
| 2012/0215200 A1* | 8/2012 | Matsuura | A61M 5/3129 604/152 |

(Continued)

FOREIGN PATENT DOCUMENTS

WO WO-2010009307 A2 * 1/2010 ................ B01L 3/00

OTHER PUBLICATIONS

Huh et al. "Reconstituting Organ-Level Lung Functions on a Chip" Science vol. 328, pp. 1662-1668, 2010.

(Continued)

*Primary Examiner* — Liban M Hassan
(74) *Attorney, Agent, or Firm* — Cesari & McKenna, LLP

(57) ABSTRACT

A biomimetic system is provided for evaluating an effect of a test sample in vitro, and includes at least one organ chip, at least one medium container, a liquid pump, a nebulizer, a gas pump, and a chamber device. The liquid pump is provided to drive a liquid medium in the medium container to flow into a lower sub-channel of the organ chip and then to be discharged back into the medium container. The nebulizer is provided for atomizing a test solution including the test sample into an aerosol. The gas pump is provided to generate a pressurized gas which force the aerosol to flow out of a chamber of the chamber device and then to flow through an upper sub-channel of the organ chip.

7 Claims, 5 Drawing Sheets

(56) References Cited

U.S. PATENT DOCUMENTS

2014/0158233 A1* 6/2014 Leslie .................... C12M 29/00
                                                        137/561 R

OTHER PUBLICATIONS

Benam et al., "Small airway-on-a-chip enables analysis of human lung inflammation and drug responses in vitro", Nature Methods vol. 13, pp. 151-160, Advanced Online Publication doi:10.1038/nmeth.3697, available online Dec. 21, 2015.

* cited by examiner

BIOMIMETIC SYSTEM

CROSS-REFERENCE TO RELATED APPLICATION

This application claims priority from Taiwanese invention patent application no. 109103354, filed on Feb. 4, 2020.

FIELD

The disclosure relates to a biomimetic system, more particularly to a biomimetic system for evaluating an effect of a test sample in vitro.

BACKGROUND

To serve as alternatives to animal testing, many conventional biomimetic systems are developed for evaluating the effect of chemical substances (such as nicotine) on the lung function. However, for some of the conventional biomimetic systems in which the chemical substances suspended in the air are transferred to cells of a lung organ chip in the liquid form, it may be difficult to simulate the true effect of the chemical substances on the cells in the human lung.

SUMMARY

Therefore, an object of the disclosure is to provide a biomimetic system for evaluating an effect of a test sample in vitro.

According to the disclosure, a biomimetic system is provided for evaluating an effect of a test sample in vitro, and includes at least one organ chip, at least one medium container, a liquid pump, a nebulizer, a gas pump, and a chamber device. The organ chip includes an upper substrate, a lower substrate which defines a channel together with the upper substrate, and a porous membrane which is disposed between the upper and lower substrates to divide the channel into an upper sub-channel and a lower sub-channel. The porous membrane has an upward surface positioned in the upper sub-channel for adhering of epithelium cells, and a downward surface positioned in the lower sub-channel for adhering of endothelial cells. The medium container is configured for containing therein a liquid medium, and is in fluid communication with a liquid outlet for the lower sub-channel. The liquid pump has a pump inlet and a pump outlet. The pump inlet is coupled to the medium container to permit the liquid medium to be drawn out by the liquid pump from the medium container. The pump outlet is coupled to a liquid inlet for the lower sub-channel so as to permit the liquid medium to be driven by the liquid pump to flow into the lower sub-channel and then to be discharged back into the medium container to thereby circularly supply the liquid medium to the lower sub-channel for providing nutrition to the epithelium cells and the endothelial cells. The nebulizer is provided for atomizing a test solution including the test sample into an aerosol. The gas pump is coupled upstream of the upper sub-channel for supplying a pressurized gas. The chamber device defines therein a chamber, and has an aerosol inlet, at least one outlet port, and at least one inlet port. The aerosol inlet is disposed upstream of the chamber and is coupled downstream of the nebulizer so as to permit the aerosol from the nebulizer to be introduced into the chamber. The outlet port is disposed downstream of the chamber and is coupled upstream of a gas inlet for the upper sub-channel. The inlet port is disposed upstream of the chamber and downstream of the gas pump for introducing the pressurized gas into the chamber, and is positioned to permit the aerosol to be forced by the pressurized gas to flow out of the chamber into the upper sub-channel through the outlet port.

With the provision of the biomimetic system of the disclosure, the test sample in the form of aerosol is forced by the pressured gas, rather than a liquid, to be brought into contact with the epithelium cells in the upper sub-channel of the organ chip. In addition, the liquid medium is forced to flow through the lower sub-channel to provide nutrition to the epithelium cells and the endothelial cells of the organ chip. Therefore, the biomimetic system is useful in determining the effect of the test sample on the cells inside the organ chip in a more realistic way.

BRIEF DESCRIPTION OF THE DRAWINGS

Other features and advantages of the disclosure will become apparent in the following detailed description of the embodiment(s) with reference to the accompanying drawings, in which.

DETAILED DESCRIPTION

Figure 1:
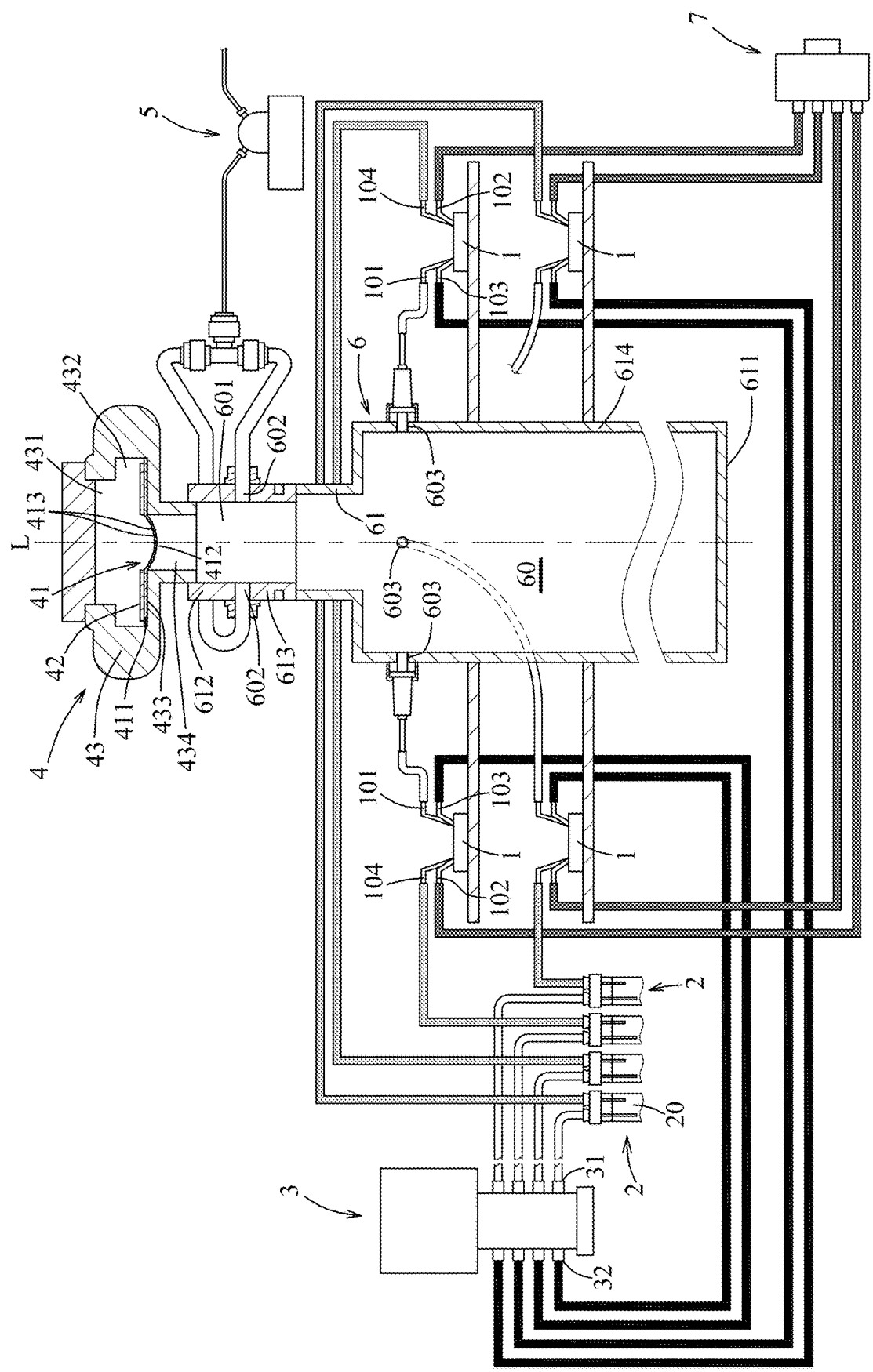
FIG. 1 is a fragmentary, partial, schematic cross-sectional view of a biomimetic system according to an embodiment of the disclosure.

Before the disclosure is described in greater detail, it should be noted that where considered appropriate, reference numerals have been repeated among the figures to indicate corresponding or analogous elements, which may optionally have similar characteristics.

To aid in describing the disclosure, directional terms may be used in the specification and claims to describe portions of the present disclosure (e.g., front, rear, left, right, top, bottom, etc.). These directional definitions are intended to merely assist in describing and claiming the disclosure and are not intended to limit the disclosure in any way.

As shown in FIG. 1, a biomimetic system is provided for evaluating an effect of a test sample in vitro, and includes at least one organ chip 1, at least one medium container 2, a liquid pump 3, a nebulizer 4, a gas pump 5, and a chamber device 6. The test sample may be smoke, drugs, gas, toxins, air-suspended particles, etc.

Figure 3:
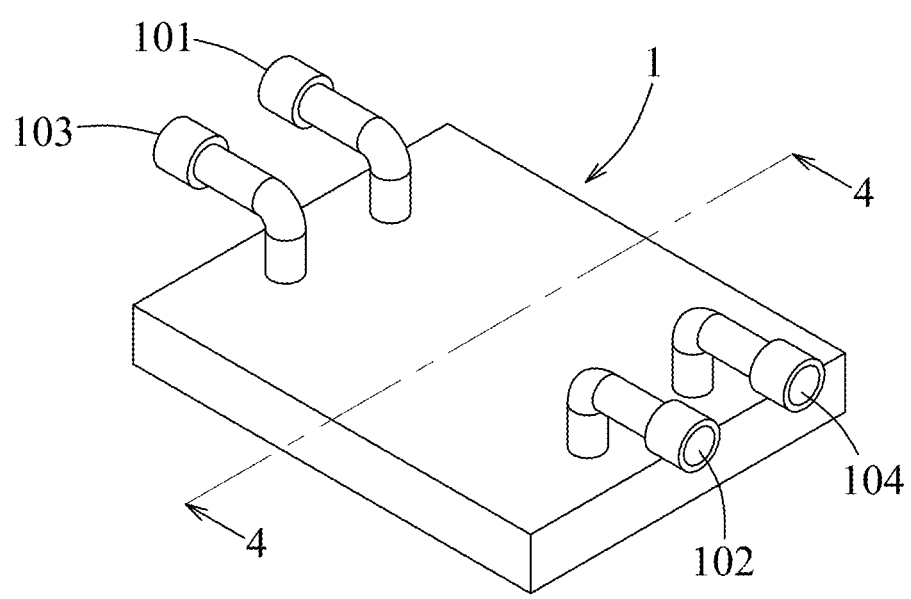
FIG. 3 is a perspective schematic view illustrating an organ chip of the biomimetic system.
Figure 4:
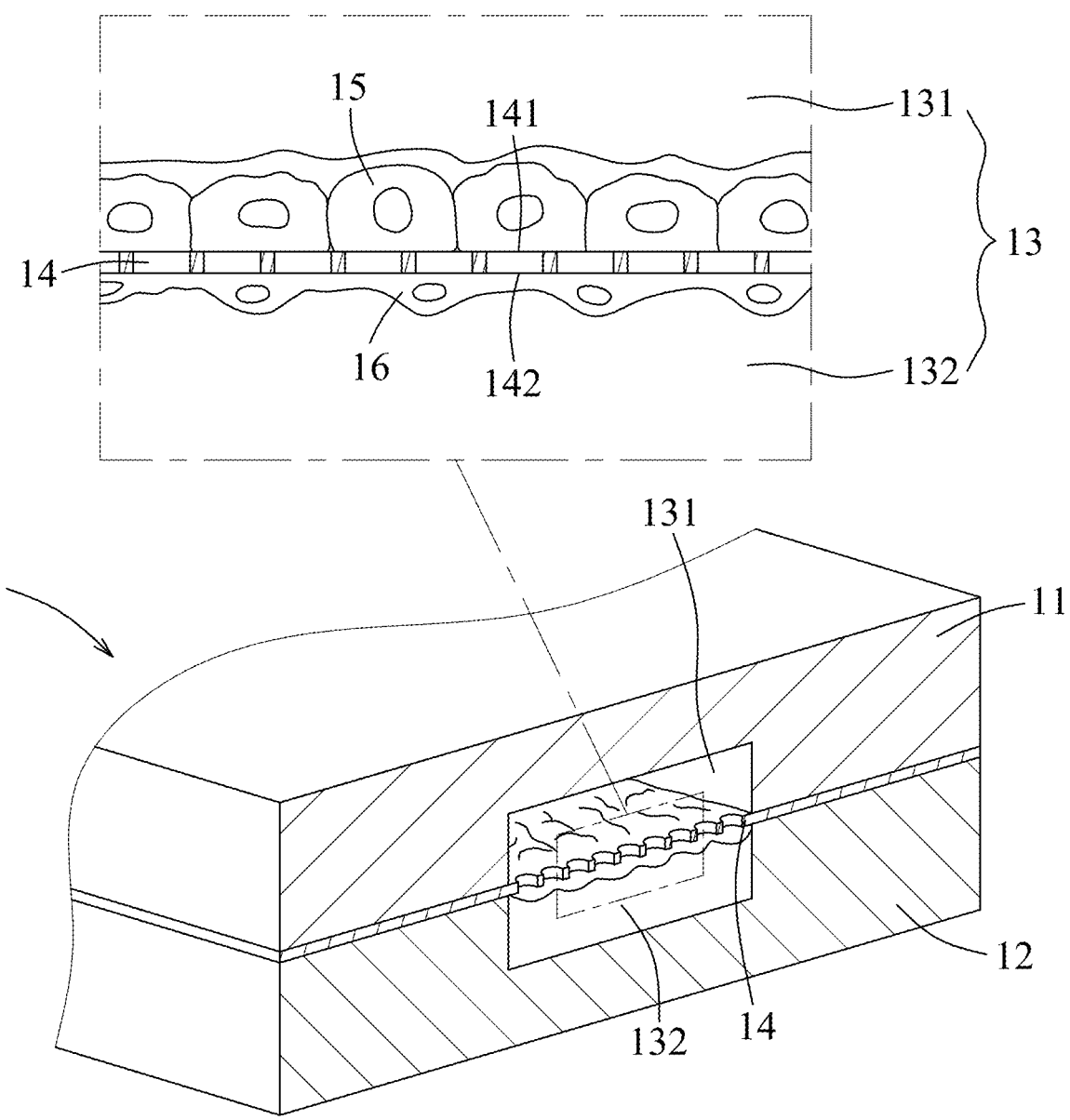
FIG. 4 is a schematic cross-sectional view of the organ chip.

As shown in FIGS. 3 and 4, the organ chip 1 includes an upper substrate 11, a lower substrate 12, and a porous membrane 14. The lower substrate 12 defines a channel 13 together with the upper substrate 11. The porous membrane 14 is disposed between the upper and lower substrates 11, 12 to divide the channel 13 into an upper sub-channel 131 and a lower sub-channel 132. The porous membrane 14 has an upward surface 141 positioned in the upper sub-channel 131 for adhering of epithelium cells 15, and a downward surface 142 positioned in the lower sub-channel 132 for adhering of endothelial cells 16. In an embodiment, each of the upper and lower substrates 11, 12 may be made of polydimethylsiloxane (PDMS) and using a mold, and the porous membrane 14 may be a Transwell insert membrane (PET membrane, pore size of 0.4 microns) for a Falcon® 6-well plate.

The upper and lower substrates 11, 12 may be bonded to each other through the porous membrane 14 using a silane coupling agent to form a very stable Si—O—Si bond between the upper and lower substrates 11, 12. Therefore, the organ chip 1 is suitable for long time culture of cells. For details about bonding of the upper and lower substrates 11, 12, the article titled "Irreversible, direct bonding of nanoporous polymer membranes to PDMS or glass microdevices" (Lab Chip, 2010 Mar. 7, 10(5): 548-552) may be referenced.

Figure 5:
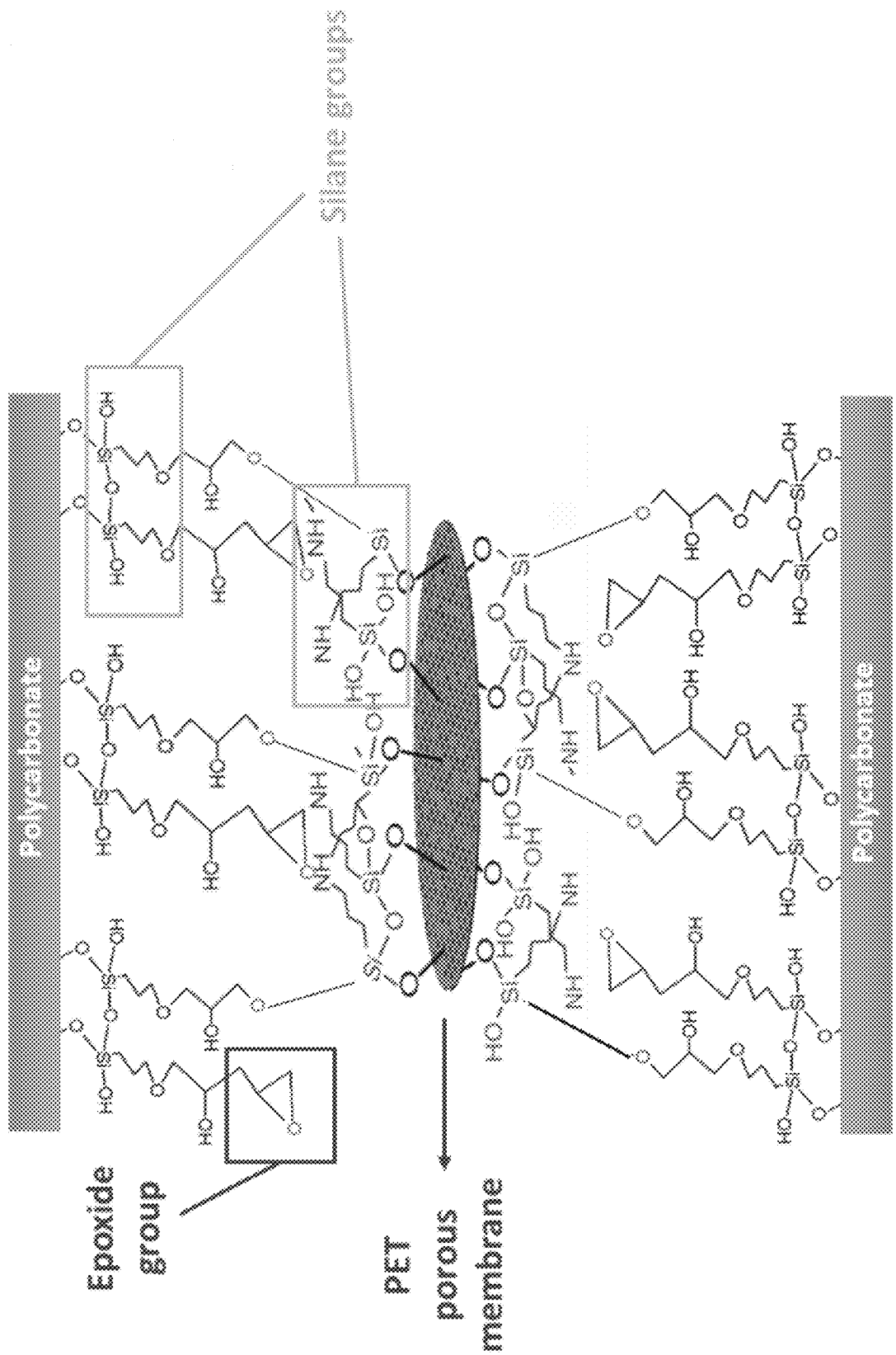
FIG. 5 is a schematic view illustrating bonding among upper and lower substrates in the organ chip.

In an embodiment shown in FIG. 5, each of the upper and lower substrates 11, 12 may be made of polycarbonates (PC), and the upper and lower substrates 11, 12 may be bonded to each other through the porous membrane 14 (which is made of PET) using the silane coupling agent. In addition, each of the upper and lower substrates 11, 12 is bonded to the porous membrane 14 via silane groups and epoxide groups.

The medium container 2 is configured for containing therein a liquid medium 20, and is in fluid communication with a liquid outlet 104 for the lower sub-channel 132.

The liquid pump 3 has a pump inlet 31 and a pump outlet 32. The pump inlet 31 is coupled to the medium container 2 to permit the liquid medium 20 to be drawn out by the liquid pump 3 from the medium container 2. The pump outlet 32 is coupled to a liquid inlet 103 for the lower sub-channel 132 so as to permit the liquid medium 20 to be driven by the liquid pump 3 to flow into the lower sub-channel 132 and then to be discharged back into the medium container 2 to thereby circularly supply the liquid medium 20 to the lower sub-channel 132 for providing nutrition to the epithelium cells 15 and the endothelial cells 16. In an embodiment, the liquid pump 3 may be a peristaltic pump.

The nebulizer 4 is provided for atomizing a test solution including the test sample into an aerosol.

Figure 2:
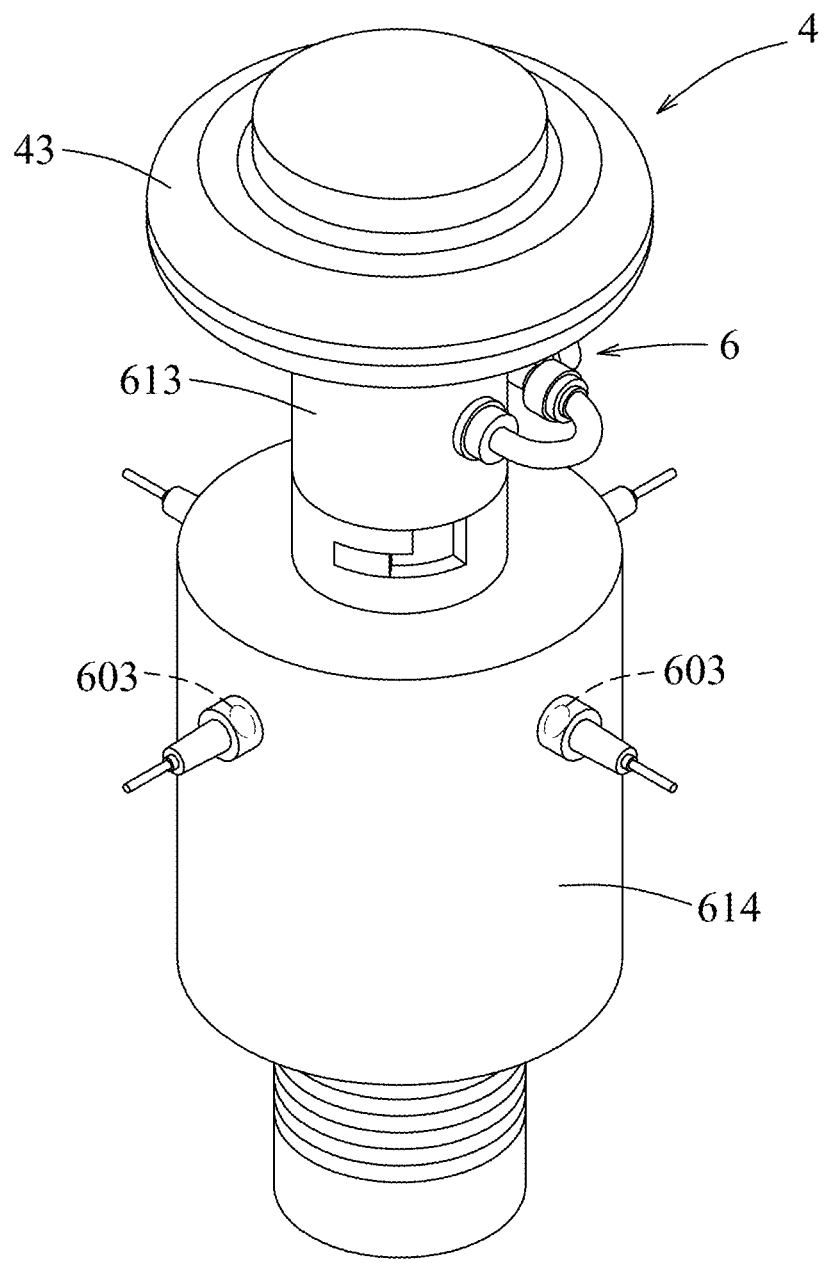
FIG. 2 is perspective schematic view illustrating a nebulizer and a chamber device of the biomimetic system.

In an embodiment shown in FIGS. 1 and 2, the nebulizer 4 may include a vibratable piece 41 and a piezoelectric piece 42. The vibratable piece 41 is configured to permit the test solution to be placed thereon, and includes a peripheral segment 411 and a central segment 412 which is surrounded by the peripheral segment 411, and which is formed with a plurality of apertures 413 each tapering downwardly. The piezoelectric piece 42 is coupled on the peripheral segment 411 such that when a current is applied to the piezoelectric piece 42, the vibratable member 41 is driven to vibrate to cause the test solution passing through the apertures 413 to be atomized into the aerosol.

In an embodiment shown in FIGS. 1 and 2, the nebulizer 4 may further include a casing 43 having an upper opening 431, a cavity 432 extending downwardly from the upper opening 431 along a longitudinal axis (L) to terminate at a cavity bottom 433, and a communication port 434 extending downwardly from the cavity bottom 433. The vibratable piece 41 is disposed on the cavity bottom 433 to permit the central segment 412 of the vibratable piece 41 to be in register with the communication port 434 to thereby allow the aerosol to spray out of the casing 43 from the communication port 434.

The gas pump 5 is coupled upstream of the upper sub-channel 131 for supplying a pressurized gas.

As shown in FIGS. 1 and 2, the chamber device 6 defines therein a chamber 60, and has an aerosol inlet 601, at least one inlet port 602, and at least one outlet port 603. The aerosol inlet 601 is disposed upstream of the chamber 60 and is coupled downstream of the nebulizer 4 so as to permit the aerosol from the nebulizer 4 to be introduced into the chamber 60. The outlet port 603 is disposed downstream of the chamber 60 and is coupled upstream of a gas inlet 101 for the upper sub-channel 131. The inlet port 602 is disposed upstream of the chamber 60 and downstream of the gas pump 5 for introducing the pressurized gas into the chamber 60, and is positioned to permit the aerosol to be forced by the pressurized gas to flow out of the chamber 60 into the upper sub-channel 131 through the outlet port 603.

Therefore, for a period of time after culturing the cells 15, 16 in the organ chip 1 by providing the liquid medium 20 to circularly and continuously flow through the lower sub-channel 132, and after continuously applying the aerosol including the test sample to the upper sub-channel 131, the effect of the test sample on the cells 15, 16 inside the organ chip 1 may be determined. In the case that the cells 15, 16 are human lung epithelium cells and human lung endothelial cells, respectively, the organ chip 1 may be used for simulating the effect of the test sample on the cells inside a human lung. The flow rates of the liquid mediums 20, aerosol, and the pressurized gas may be controlled using a computer program (not shown) to permit the upper and lower sub-channels 131, 132 of the organ chip 1 to have flow rates respectively simulating a gas flow rate and a liquid flow rate in a human pulmonary alveolus.

In an embodiment shown in FIGS. 1 and 2, the biomimetic system may include a plurality of the organ chips 1, and a plurality of the medium containers 2 that are coupled for receiving the liquid mediums 20 from the liquid outlets 104 for the lower sub-channels 132 of the organ chips 1, respectively.

In addition, the liquid pump 3 may have a plurality of the pump inlets 31 which are coupled respectively to the medium containers 2, and a plurality of the pump outlets 32 which are coupled respectively to the liquid inlets 103 for the lower sub-channels 132 of the organ chips 1.

The chamber device 6 may have a plurality of the outlet ports 603 which are coupled respectively to the gas inlets 101 for the upper sub-channels 131 of the organ chips 1 so as to permit the aerosol entrained in the pressurized gas to be evenly distributed into the upper sub-channels 131 of the organ chips 1. Further, the chamber device 6 may have a plurality of the inlet ports 602.

In an embodiment shown in FIGS. 1 and 2, the chamber device 6 may have a surrounding wall 61 which extends about a longitudinal axis (L) to define therein the chamber 60, and which further extends along the longitudinal axis (L) to terminate at a lower closed end 611 and an upper open end 612 that defines the aerosol inlet 601. The surrounding wall 61 has an upper wall segment 613 and a lower wall segment 614 which has a dimension larger than that of the upper wall segment 613. The inlet ports 602 extend radially through the upper wall segment 613 to be angularly displaced about the longitudinal axis (L), and the outlet ports 603 extend radially through the lower wall segment 614 to be angularly displaced about the longitudinal axis (L).

In an embodiment shown in FIG. 1, the biomimetic system according to claim 1 may further include a filter 7 which is coupled downstream of a gas outlet 102 for the upper sub-channel 131 of each of the organ chips 1 for filtering the gas discharged from the gas outlet 102 for the upper sub-channel 131 of each of the organ chips 1.

In sum, as an alternative to animal testing, the biomimetic system of the disclosure may be useful in determining the effect of the test sample on the human or animal cells inside the organ chip in a more realistic way, and may be advantageous for studying human or animal disease and developing new drugs.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A biomimetic system for evaluating an effect of a test sample in vitro, said biomimetic system comprising:
   at least one organ chip including an upper substrate, a lower substrate which defines a channel together with said upper substrate, and a porous membrane which is disposed between said upper and lower substrates to divide said channel into an upper sub-channel and a lower sub-channel, said porous membrane having an upward surface facing said upper sub-channel for adhering of epithelium cells, and a downward surface facing said lower sub-channel for adhering of endothelial cells;
   at least one medium container which is configured for containing therein a liquid medium, and which is in fluid communication with a liquid outlet for said lower sub-channel of said at least one organ chip;
   a liquid pump having
      at least one pump inlet coupled to said at least one medium container to permit the liquid medium to be drawn out by said liquid pump from said at least one medium container, and
      at least one pump outlet coupled to a liquid inlet for said lower sub-channel of said at least one organ chip so as to permit the liquid medium to be driven by said liquid pump to flow into said lower sub-channel of said at least one organ chip and then to be discharged back into said at least one medium container to thereby circularly supply the liquid medium to said lower sub-channel of said at least one organ chip for providing nutrition to the epithelium cells and the endothelial cells;
   a nebulizer for atomizing a test solution including the test sample into an aerosol;
   a gas pump disposed upstream of said upper sub-channel of said at least one organ chip for supplying a pressurized gas; and
   a chamber device defining therein a chamber, and having
      an aerosol inlet wall defining an aerosol inlet having an upper open end and a lower open end, wherein said aerosol inlet is disposed upstream of said chamber and downstream of said nebulizer so as to permit the aerosol from said nebulizer to be introduced into said chamber,
      at least one outlet port which is disposed downstream of said chamber and which is disposed upstream of a gas inlet for said upper sub-channel of said at least one organ chip, and
      at least one inlet port which is disposed upstream of said chamber and downstream of said gas pump for introducing the pressurized gas into said chamber, and which is positioned to permit the aerosol to be forced by the pressurized gas to flow out of said chamber into said upper sub-channel of said at least one organ chip through said at least one outlet port, wherein said at least one inlet port is formed in said aerosol inlet wall of said chamber device and is disposed downstream of said upper open end and upstream of said lower open end of said aerosol inlet.

2. The biomimetic system according to claim 1, wherein said at least one organ chip comprises a plurality of organ chips;
   said at least one medium container comprises a plurality of medium containers, each of which is configured for receiving the liquid medium from said liquid outlet for said lower sub-channel of a respective one of said organ chips;
   said at least one pump inlet comprises a plurality of pump inlets which are coupled respectively to said medium containers;
   said at least one pump outlet comprises a plurality of pump outlets, each of which is coupled to said liquid inlet for said lower sub-channel of a respective one of said organ chips; and
   said at least one outlet port comprises a plurality of outlet ports, each of which is coupled to said gas inlet for said upper sub-channel of a respective one of said organ chips so as to permit the aerosol entrained in the pressurized gas to be evenly distributed into the upper sub-channels of said organ chips.

3. The biomimetic system according to claim 1, wherein said liquid pump is a peristaltic pump.

4. The biomimetic system according to claim 1, further comprising a filter which is disposed downstream of a gas outlet for said upper sub-channel of said at least one organ chip for filtering the gas discharged from said gas outlet for said upper sub-channel of said at least one organ chip.

5. The biomimetic system according to claim 1, wherein said nebulizer includes
   a vibratable piece configured to permit the test solution to be placed thereon, and including a peripheral segment and a central segment which is surrounded by said peripheral segment, and which is formed with a plurality of apertures each tapering downwardly, and
   a piezoelectric piece coupled on said peripheral segment such that when a current is applied to said piezoelectric piece, said vibratable member is driven to vibrate to cause the test solution passing through said apertures to be atomized into the aerosol.

6. The biomimetic system according to claim 5, wherein said nebulizer further includes a casing having an upper opening, a cavity extending downwardly from said upper opening along a longitudinal axis to terminate at a cavity bottom, and a communication port extending downwardly from said cavity bottom, said vibratable piece being disposed on said cavity bottom to permit said central segment of said vibratable piece to be in register with said communication port to thereby allow the aerosol to spray out of said casing from said communication port.

7. The biomimetic system according to claim 2, wherein said chamber device has a surrounding wall which extends about a longitudinal axis to define therein said chamber, and which further extends along the longitudinal axis to terminate at a lower closed end and the upper open end, said surrounding wall having an upper wall segment that defines said aerosol inlet wall and a lower wall segment which has a dimension larger than that of said upper wall segment, said at least one inlet port extending radially through said upper wall segment, said outlet ports extending radially through said lower wall segment to be angularly displaced about the longitudinal axis.

\* \* \* \* \*